Figure 1:
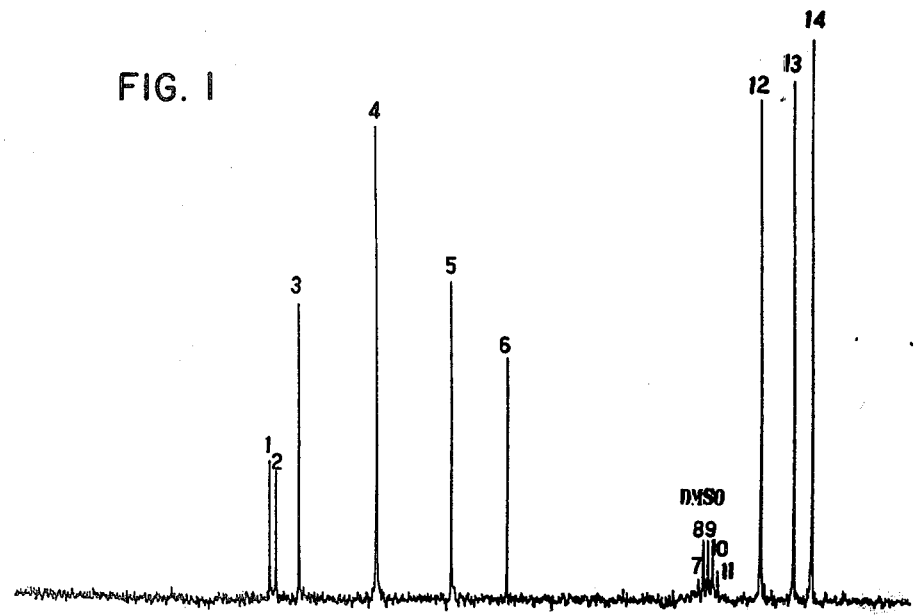

United States Patent [19]

Hamano et al.

[11] 4,180,577
[45] Dec. 25, 1979

[54] FURO[2,3d]PYRIMIDINE DERIVATIVES AND ANTI-ULCER CONTAINING THE SAME

[75] Inventors: Sachiyuki Hamano, Tokyo; Takaharu Nakamura, Chiba, both of Japan

[73] Assignee: Eisai Co., Ltd., Tokyo, Japan

[21] Appl. No.: 902,833

[22] Filed: May 2, 1978

Related U.S. Application Data

[63] Continuation-in-part of Ser. No. 829,862, Sep. 1, 1977, abandoned, which is a continuation of Ser. No. 739,449, Nov. 5, 1976, abandoned, which is a continuation of Ser. No. 557,889, Mar. 12, 1975, abandoned.

[30] Foreign Application Priority Data

Mar. 14, 1974 [JP] Japan .................................. 49-28628

[51] Int. Cl.² .................. A61K 31/505; C07D 491/04
[52] U.S. Cl. .................................. 424/251; 544/278; 544/281
[58] Field of Search .................. 544/278; 424/251

[56] References Cited

U.S. PATENT DOCUMENTS 3,632,763  1/1972  Hess ..................................... 424/251
4,031,089  6/1977  Fauran ..................... 260/247.5 DP

FOREIGN PATENT DOCUMENTS 1288878  2/1978  Japan .
1500962  2/1978  United Kingdom .

*Primary Examiner*—Donald G. Daus
*Assistant Examiner*—Lisa Jones
*Attorney, Agent, or Firm*—Wenderoth, Lind & Ponack

[57] ABSTRACT

New furo[2, 3d]pyrimidine derivatives of the general formula:

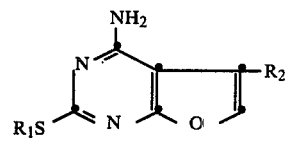

wherein $R_1$ represents a lower alkyl, a lower alkenyl or an aralkyl group, and $R_2$ represents a lower alkyl, unsubstituted phenyl, carboxyl, methylsulphonyl, methoxycarbonyl or a nitro-substituted phenyl group, or the corresponding pharmacologically acceptable acid addition salts. The new compounds exhibit the outstanding anti-ulcer, anti-inflammatory and anti-edema effects.

18 Claims, 2 Drawing Figures

FURO[2,3d]PYRIMIDINE DERIVATIVES AND ANTI-ULCER CONTAINING THE SAME

This application is a continuation-in-part of application Ser. No. 829,862, filed Sept. 1, 1977 (now abandoned), which application is in turn a continuation of application Ser. No. 739,449, filed Nov. 5, 1976 (now abandoned), said latter application in turn being a continuation of application Ser. No. 557,889, filed Mar. 12, 1975 (now abandoned).

The present invention relates to furo[2, 3d]pyrimidine derivatives having the general formula (I)

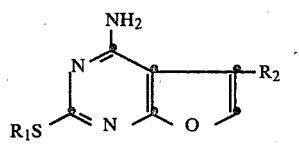

wherein $R_1$ represents a lower alkyl, a lower alkenyl or an aralkyl group, and $R_2$ represents a lower alkyl, unsubstituted phenyl, carboxyl, methylsulphonyl, methoxycarbonyl or a nitro-substituted phenyl group, or the corresponding pharmacologically acceptable acid addition salts, and anti-ulcer containing them.

As pharmacologically acceptable acid addition salts of the new compound of the present invention, there are mentioned, as a salt of an inorganic acid, for example, hydrochloride, hydrobromide, sulfate and the like; and as a salt of an organic acid, for instance, acetate, oxalate, citrate, tartarate, fumarate, and the like. A lower alkyl group in the compound of the present invention includes an alkyl group having 1–4 carbon atoms such as methyl, ethyl, propyl, isopropyl, butyl, isobutyl, and the like; and a lower alkenyl group in the present invention includes an alkenyl group having 2–4 carbon atoms such as aryl, β-aryl, butenyl, and the like. As an aralkyl group, there are mentioned benzyl, phenethyl, phenylpropyl, and the like, for example.

The new compounds according to the present invention and their pharmacologically acceptable acid addition salts exhibit the outstanding anti-ulcer, anti-inflamatory and anti-edema effects.

The compound of the present invention represented by the general formula (I) is, for example, synthesized by the following reaction schema:

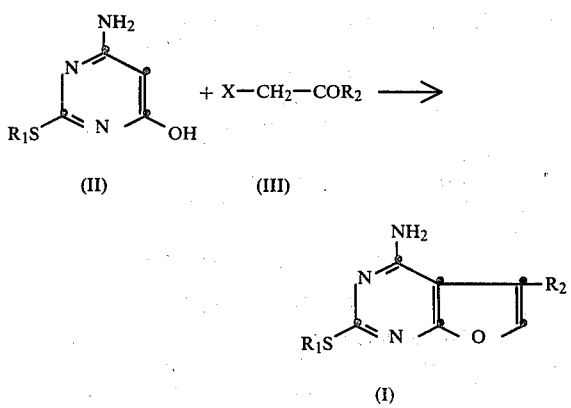

In the above formulae (I), (II) and (III), $R_1$ and $R_2$ have the same meanings as defined above, and X represents a halogen atom.

As shown in the above reaction schema, the process of the present invention comprises reacting under heat a 2-substituted mercapto-4-amino-6-hydroxy-pyrimidine of the general formula (II) with an ω-halo-ketone of the general formula (III) to obtain the contemplated compound of the general formula (I).

Although the reaction can be carried out in the absence of a solvent, it is preferable to use an appropriate organic solvent, especially a polar solvent such as 1,2-dimethoxyethane, dimethyl formamide, and the like, because the use of the solvent facilitates the reaction, and also the subsequent treatments can be easily carried out.

In the original U.S. patent application Ser. Nos. 557,889; 739,449; and 829,862, the inventors considered that the compound to be produced is imidazo-[1, 2C]pyrimidine derivative of the general formula (IV):

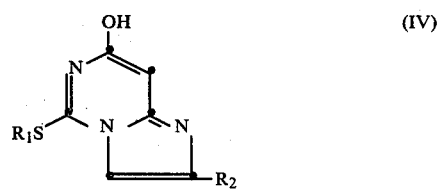

wherein $R_1$ and $R_2$ have the same meanings as defined above.

As a result of subsequent study of the chemical structure of the compound produced by the process of the present application, however, the inventors have confirmed that the contemplated compound is not represented by the formula (IV), but furo[2, 3d]pyrimidine derivative of the general formula (I)

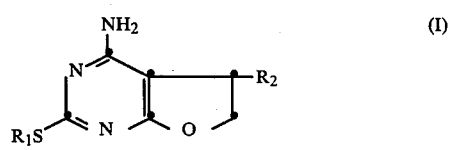

wherein $R_1$ and $R_2$ have the same meanings as defined above.

The chemical structures of the compound represented by the general formula (I) were determined by comfirming the existence of a primary amine (—NH$_2$) by the N-substituted phthalimide method and the like, and determining the position of $R_2$ (having the same meanings as mentioned above) by $^{13}$C-NMR.

Concrete experiment is explained in detail in SYNTHESIS EXAMPLE 1 as described later with respect to synthesis of 2-ethylmercapto-4-amino-5-methyl-furo[2, 3d]pyrimidine which was produced by reacting 2-ethylmercapto-4-amino-6-hydroxy-pyrimidine with bromoacetone.

The illustrative of the compounds represented by the general formula (I) are shown in Table 1.

Table 1

| Symbols of Compound | R₁ | R₂ | MolecularFormula Melting Point (°C.) | Elementary Analysis | | | | | |
|---|---|---|---|---|---|---|---|---|---|
| | | | | Calculated (%) | | | Found (%) | | |
| | | | | C | H | N | C | H | N |
| A | —C$_2$H$_5$ | —CH$_3$ | C$_9$H$_{11}$N$_3$OS · HBr<br>215°–217°* | 37.24 | 4.17 | 14.48 | 37.57 | 4.02 | 14.23 |
| B | —CH$_3$ | —CH$_3$ | C$_8$H$_9$N$_3$OS · HBr<br>263°–4°* | 34.79 | 3.66 | 15.22 | 35.15 | 3.77 | 15.34 |
| C | —CH$_2$CH=CH$_2$ | —CH$_3$ | C$_{10}$H$_{11}$N$_3$OS<br>262°–3°* | 54.29 | 5.01 | 19.00 | 53.92 | 5.27 | 18.59 |
| D | n C$_4$H$_9$— | —CH$_3$ | C$_{11}$H$_{15}$N$_3$OS<br>120°–122° | 55.68 | 6.37 | 17.71 | 55.63 | 6.37 | 17.66 |
| E | CH$_3$— | NO$_2$— | C$_{13}$H$_{10}$N$_4$O$_3$S<br>201°–203° | 51.66 | 3.34 | 18.54 | 51.24 | 3.23 | 18.17 |
| F | —CH$_2$ | —CH$_3$ | C$_{14}$H$_{13}$N$_3$OS<br>175°–7° | 61.96 | 4.84 | 15.49 | 61.84 | 4.81 | 15.37 |
| G | —(CH$_2$)$_2$ | —CH$_3$ | C$_{15}$H$_{15}$N$_3$OS · HBr<br>227°–8° | 49.18 | 4.40 | 11.47 | 49.24 | 4.47 | 11.60 |
| H | —CH$_3$ |  | C$_{13}$H$_{11}$N$_3$OS<br>171°–3° | 60.69 | 4.31 | 16.34 | 60.86 | 4.39 | 16.29 |
| I | —CH$_3$ | —SO$_2$CH$_3$ | C$_{14}$H$_{13}$N$_3$O$_3$S$_2$<br>203°–4° | 50.13 | 3.91 | 12.53 | 50.09 | 3.86 | 12.60 |
| J | —CH$_3$ | —COOCH$_3$ | C$_{15}$N$_{13}$N$_3$O$_3$S<br>220°–2° | 57.14 | 4.16 | 13.33 | 57.00 | 4.13 | 13.35 |
| K | —CH$_3$ | —COOH | C$_{14}$H$_{11}$N$_3$O$_3$S · ½H$_2$O<br>263°–5°* | 54.18 | 3.89 | 13.53 | 54.58 | 3.81 | 13.81 |
| L | —C$_2$H$_5$ |  | C$_{14}$H$_{13}$N$_3$OS<br>135°–5° | 61.98 | 4.83 | 15.49 | 62.19 | 4.69 | 15.47 |
| M | —C$_2$H$_4$ | —SO$_2$CH$_3$ | C$_{15}$H$_{15}$N$_3$O$_3$S$_2$<br>178°–180° | 51.58 | 4.33 | 12.03 | 51.49 | 4.31 | 12.01 |

*With decomposition

The compounds (I) according to the present invention have an outstanding anti-ulcer effect. This is certified by the results of the following pharmacological experiments.

Compounds to be Tested

2-Ethylmercapto-4-amino-5-methyl-furo[2,3d]pyrimidine hydrobromide . . . (hereinafter referred to the compound A of this invention)

2-Methylmercapto-4-amino-5-methyl-furo[2,3d]pyrimidine hydrobromide . . . (hereinafter referred to the compound B of this invention)

2-Allylmercapto-4-amino-5-methyl-furo[2,3d]pyrimidine . . . (hereinafter referred to the compound C of this invention)

Medicines Used and the Amount Thereof

The compounds to be tested were suspended in 5% serous gum arabic solution, so as to adjust their concentration to 0.5 ml/100 g B.W. for oral administration, or 0.2 ml/100 g B.W. for duodenum administration. Indomethacin, [1-(p-chlorobenzoyl)-5-methoxy-2-methylindole-3-acetic acid] for control was suspended in 5% serous gum arabic solution, so as to adjust its concentration to 0.5 ml/100 g B.W.

PHARMACOLOGICAL EXPERIMENT 1

Effect for Secretion of Gastric Juice

According to the method by H. Shay et al [Gastroenterology 5, 43 (1945)], male rats (weighing about 320 g) of SD strain were fasted for 24 hours, and then incised their bellys under the ether rausch anesthesia, and finally ligatured the pylouruses. The solutions of the compounds to be tested were adjusted to pH 5.0, and administered into the duodenum. The bellys were closed. After 4 hours, the animals were slaughtered by anesthesia, and the gastric juice was collected.

The volume of the gastric juice was measured and titrated by N/50 NaOH solution with Töpfer indicator and phenolphthalein indicator, to determine the free acid output the total acid output, respectively.

Results of Experiments

Table 2 shows the effects for secretion of the gastric juice, that is, an amount of the gastric juice, a free acid output, and a total acid output, of the rats, in case the compounds to be tested are used.

Table 2

| Compounds to be tested | Dose (mg/Kg) | Number of rats | Amount of gastric juice Vol. (ml)/100g B.W. | Free Acid Output μEq/100g B.W. | Total Acid Output μEq/100g B.W. |
|---|---|---|---|---|---|
| Control | — | 7 | 1.78 ± 0.26 | 133.2 ± 32.7 | 154.0 ± 36.0 |
| Compound A of this invention | 100 | 6 | 0.81 ± 0.15** | 41.0 ± 16.6* | 65.8 ± 20.4 |
| Compound B of this invention | 100 | 7 | 0.51 ± 0.09** | 16.5 ± 5.5** | 37.8 ± 5.6** |
| Compound C of this invention | 100 | 6 | 0.49 ± 0.11** | 18.2 ± 7.1** | 33.1 ± 7.6** |

\* : $P<0.05$
\*\* : $P<0.01$ (t-test)

The compounds to be tested were administered into the duodenum immediately after ligaturing the pylorus.

The medicine solution was adjusted to pH 5.0 with N—NaOH solution.

The compounds A, B and C of this invention suppressed over 54% of the amount of the gastric juice, over 69% of the free acid output and over 57% of the total acid output, for the compound of the control group.

PHARMACOLOGICAL EXPERIMENT 2

Effect on Ligature Ulcer of the Pylorus

According to the method by H. Shay et al. [Gastroenterology 5, 43 (1945)], male rats (weighing about 320 g) of SD strain were fasted for 24 hours, and then incised the belly under the ether rausch anesthesia, and finally ligatured the pyloruses. The solution of compounds to be tested were adjusted to pH 5.0, and administered into the duodenum. The bellys were closed. After subsequent 17 hours, the animals were slaughtered by the anesthesia, and their stomaches were extirpated. More particularly, the stomaches were incised along the greater curvature. The ulcer generated at forestomach was ranged as shown in the following. The total of the ranking was named as the ulcer index.

| Size of ulcer (long diameter) | Ranking |
|---|---|
| Not greater than 1 mm | 1 |
| Greater than 1 mm, but not greater than 3 mm | 2 |
| Greater than 3 mm, but not greater than 5 mm | 3 |
| Greater than 5 mm, but not greater than 8 mm | 4 |
| Greater than 8 mm | 5 |

Results of Experiment

Table 3 shows the effects for ligature ulcer of the pylorus.

Table 3

| Compounds to be tested | Dose (mg/Kg) | Number of Rats | Ulcer index (mm) | Percentage of inhibition (%) |
|---|---|---|---|---|
| Control | — | 6 | 54 ± 14 | — |
| Compound A of this invention | 300 | 4 | 0 ± 0** | 100 |

\*\* : $P<0.01$ (t-test)

When 300 mg/Kg of the compound A of this invention were administered, the inhibition was 100% for the ulcer index of the control group.

PHARMACOLOGICAL EXPERIMENT 3

Inhibitory Effects on the Immersive Stress-induced Ulcer

According to the method by K. Takagi et al. [Jap. J. Pharmacol. 18, 9 )1968)], female rats (weighing about 160 g) of SD strain were put in a cage made of wire gauze for restraint, dipped in a water bath at the temperature of 23° C. so as to cover the lower end of their breast bones, and allowed to stand for 20 hours. The animals were then slaughtered by the anesthesia, and their stomaches were extirpated. The stomaches were inflated with 10 ml of physiological saline water, and dipped in 0.5% neutral formalin solution for about 5 minutes according to the method by D. A. Brodie et al [Gastroenterology 38, 354–360 (1960)]. The stomaches were then incised along the greater curvature. The length of each ulcer (erosion) generated at adenostomach was measured. The total of said lengthes were assigned as the ulcer index.

The compounds to be tested were orally administered prior to the immersion.

Results of Experiment

The inhibitory effect for immersive strees-induced ulcer are shown in Table 4.

Table 4

| Compounds to be tested | Dose (mg/Kg) | Number of Rats | Ulcer index (mm) | Percentage of inhibition (%) |
|---|---|---|---|---|
| Control | — | 6 | 80.4 ± 3.5 | — |
| Compound A of this invention | 150 | 6 | 63.5 ± 6.5* | 21.0 |
| Compound A of this invention | 300 | 6 | 49.3 ± 3.4** | 38.7 |

\* : $P < 0.05$
\*\* : $P < 0.01$ (t-test)

When 150 mg/Kg of the compound A of this invention are used, the suppression was 21.0% for the ulcer index of the control, and when 300 mg/Kg were used, the inhibition was 38.7%. It was thus confirmed that there is a dose dependent manner of the compound A.

PHARMACOLOGICAL EXPERIMENT 4

Inhibitory Effects on Cold-restraint Stress Induced Ulcer

This experiment was effected by referring to the method by S. Dai et al. [Eur. J. Pharmaco. 26, 15–21 (1974)] and the method by M. M. Goldenberg et al. [Am. J. Dic. Dis 19, 4, 353–360 (1974)].

Female rats of SD strain (weighing about 180 g) were restrained in a cage made of wire gauze, and the cage was allowed to stand in a room at the low temperature at 4° C. for two hours. After subsequent two hours, the animals were slaughtered. The stomaches were extirpated. Thereafter, the subsequent procedure was carried out in accordance with the pharmacological experiment 3.

The compounds to be tested were orally administered 30 minutes prior to exposure of the stress.

Results of Experiment

The effects for the cold-restraint stress induced ulcer are shown in Table 5.

Table 5

| Compounds to be tested | Dose (mg/Kg) | Number of Rats | Ulcer index (mm) | Percentage of inhibition (%) |
|---|---|---|---|---|
| Control | — | 10 | 14.8 ± 1.7 | — |
| Compound A of this invention | 50 | 10 | 3.2 ± 1.0* | 78.4 |
| Compound A of this invention | 100 | 10 | 2.1 ± 0.6* | 85.8 |

*: $P < 0.01$ (t-test)

When 50 mg/Kg of the compound of this invention were used, the inhibition was 78% for the ulcer index of the control group, and when 100 mg/Kg of the compound A were used, the inhibition was 86%. This shows that there is a dose dependent manner of the compound A.

PHARMACOLOGICAL EXPERIMENT 5

Effects on Indomethacin-induced Ulcer

Wister strain male rats (weighing about 230 g) were subjected to the fast for 24 hours. 40 mg/Kg of the Indomethacin were orally administered, respectively. After 4 hours from the administration, the animals were slaughtered and their stomaches were extirpated. The subsequent procedures were carried out in accordance with the pharmacological experiment 3.

The compounds to be tested were orally administered 30 minutes prior to the administration of Indomethacin.

Results of Experiment

Table 6 shows the effects of the compound A of this invention for the stomach ulcer generated by the administration of Indomethacin.

Table 6

| Compounds to be tested | Dose (mg/Kg) | Number of Rats | Ulcer Index (mm) | Percentage of inhibition (%) | Percentage of Incidence of Ulcer (%) |
|---|---|---|---|---|---|
| Control | — | 8 | 9.30 ± 3.09 | — | 75 |
| Compound of this invention | 25 | 8 | 1.67 ± 1.00* | 82 | 38 |
| Compound of this invention | 50 | 8 | 0 ± 0** | 100 | 0 |
| Compound of this invention | 100 | 8 | 0.20 ± 0.19* | 98 | 13 |

*: $P < 0.05$
**: $P < 0.01$ (t-test)

The compound A of this invention exhibited the inhibition of 82% when 25 mg/Kg were administered; 100% when 50 mg/Kg were administered; and 98% when 100 mg/Kg were administered, respectively, for the ulcer index of the control group. The compound A of this invention exhibited incidence of the ulcer of 38% (3 examples in 8 examples) when 25 mg/Kg were administered; 0% (nil in 8 examples) when 50 mg/Kg were administered; and 13% (one example in 8 examples) when 100 mg/Kg were administered, respectively.

From the results of the above experiments, it is confirmed that the compounds of the general formula (I) represented by the compounds A, B and C of this invention exhibit an outstanding anti-ulcer effect. $LD_{50}$ in rat is greater than 5,000 mg/Kg by oral administration. Therefore, the compounds represented by the general formula (I) and their pharmacologically acceptable acid addition salts are effective as the medicines for treating the ulcer, for example, to the treatment and the prevention of the gastric ulcer, the duodenal ulcer, the gastric hyperacidity, the stomachache, the gastric catarrhal, and the like.

The compounds represented by the general formula (I) and their pharmacologically acceptable acid addition salts are administered orally or by injection and the like. For the treatment of an adult, the dose amounts to 20–2,000 mg per day. It is preferable to divisionally administer the compound at intervals of a time depending upon the symptom.

Using the compounds represented by the general formula (I) and their pharmacologically acceptable acid addition salts, the preparation for administration can be produced by any conventional process for administration. The present invention includes, therefore, also a preparation composition containing at least one of the compounds represented by the general formula (I) which are suitable for the medicine to the human body. Such composition is provided in a conventional method by using any necessary pharmaceutical carrier, or the excipient.

It is desirable to provide this composition in a form suitable for absorption from the digestion tube. The tablet and capsule for oral administration are a form for administration of the unit dose. They may contain any conventional excepients selected from the group consisting of binders, such for example, as syrup, gum arabic, gelatine, sorbitol, tragacanth gum and polyvinyl pyrolidon; excepients, such for example, as lactose, corn starch, calcium phosphate, sorbitol and glycine; lubricants, such for example as, magnesium stearate, talc, polyethylene glycol and silica; decaying agents such for example as potato starch; or acceptable wetting agents such for example as sodium lauryl suphate. The tablets may be coated by a well known method in the art. The liquid preparations for oral administration may be aqueous or oily suspension, solution, syrup, elixir agent, and the like.

Alternatively, they may be dry products which are re-dissolved in water or other suitable vehicle prior to use. Such liquid preparations may contain any conventional additives such as suspending agents, for example, sorbitol syrup, methyl cellulose, glucose/sugar syrup, gelatine, hydroxy ethylcellulose, carboxy methylcellulose, aluminum stearate gel and hydrogenated edible oil; emulsifier, for example, lecithin, sorbitane mono-oleate and gum arabic; non-aqueous vehicles, for example, almond oil, fractionated coconut oil, oily ester, propylene glycol and ethyl alcohol; antiseptics, for example, methyl p-hydroxybenzoate, propyl p-hydroxybenzoate and sorbic acid.

The composition for injection is provided in an ampoule of unit dose, or in a vessel of large dose with the antiseptics. This composition may be in a form of suspension, solution, or emulsion in an oily or aqueous vehicle, and may contain formulating agents such as suspending agent, stabilizer and/or dispersant. On the other hand, the active components may be powder which redissolves in a proper vehicle, for example, sterilized water containing no exothermic materials prior to use.

The present invention will be explained more in detail by the following synthesis of the compound represented by the general formula (I), and the preparation composition thereof.

SYNTHESIS EXAMPLE 1

Synthesis of 2-ethylmercapto-4-amino-5-methylfuro[2,3d]pyrimidine 1.69 G of 2-ethylmercapto-4-amino-6-hydroxy-pyrimidine were added to 30 ml of 1,2-dimethoxyethane, and the mixture was stirred at a room temperature to dissolve the pyrimidine. To the solution, were added 3.2 g of bromoacetone, followed by reacting for 2 hours under reflux. After the reaction was completed, the reaction mixture was allowed to cool, and the resulting crystalline mass deposited out was recovered by filtration. The crystalline mass was recrystallized from an aqueous ethanol, thereby obtaining the final product as the corresponding hydrobromide in a form of white fine powder.

Yield: 1.7 g

Melting point: 215°–217° C. (with decomposition)

Elementary analysis of the product having presumptive formula $C_9H_{11}N_3OS \cdot HBr$ gave the following:

|  | C | H | N |
|---|---|---|---|
| Calculated (%) | 37.24 | 4.17 | 14.48 |
| Found (%) | 37.57 | 4.02 | 14.23 |

Determination of the structural Formula of the Compound (1) Confirmation of —NH$_2$ group (a) Confirmation of —NH$_2$ group by means of N-substituted phthalimide method 1 G of the above-obtained compound was heated and molten at 140°–150° C. together with 0.8 g of phthalic anhydride. The heating was further continued for about 10 minutes. After the molten material was allowed to cool, there was added a small amount of ethanol, and the resulting crystalline mass was recovered by filtration. The crude substance was recrystallized from ethanol to obtain 0.6 g of whitish yellow crystalline mass.

Melting point: 189°–190° C.

Elementary analysis of the product having presumptive formula $C_{17}H_{13}N_3O_3S$ agrees with the calculated molecular weight 339.3.

Mass M+ 339

I. R. 1785 cm$^{-1}$ (W), 1723 cm$^{-1}$ (S)

The data show characteristic absorption spectrum in the imide forming a ring with five elements.

It is therefore confirmed that the compound produced with this example for synthesis possesses a primary amino group.

(b) Confirmation of —NH$_2$ group by means of method for measuring NMR spectrum

It was confirmed that the compound produced with this example for synthesis is 5- (or 6-)methyl-furo[2,3d]pyrimidine, from the facts that 1H of aromatic protone exists at 7.2 ppm by means of NMR, and 2H(S) of protone of amino group which disappears by the addition of D$_2$O exists at 6.8 ppm.

(2) Determination of Position of —CH$_3$ Group

FIG. 1 shows the data of $^{13}$C—NMR which were measured by the use of FX-60, $\delta_6$-DMSO manufactured and sold by Nippon Denshi-sha in Japan.

Figure 2:
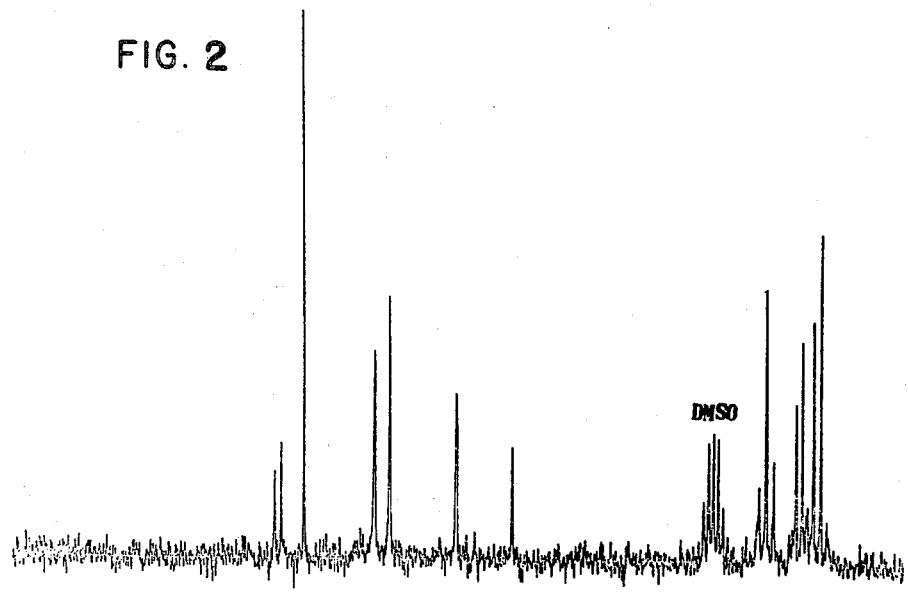

The peak No. 4 of absorption of FIG. 2 shows doublet in off-Resonance, and it is observed that there exist two absorption regions of quaternary carbon wherein the atom adjacent to a higher magnetic field than the aromatic carbon is carbon atom and three absorption regions of carbon wherein the atom adjacent to a lower magnetic field than the aromatic carbon is nitrogen or oxygen atom, whereby —CH$_3$ group is located at the 5-position.

From the foregoing confirmation test, the chemical structure of the compound prepared by this example for synthesis is 2-ethylmercapto-4-amino-5-methyl-furo[2,3d]pyrimidine.

SYNTHESIS EXAMPLE 2

Synthesis of 2-n-butylmercapto-4-amino-5-methyl-furo[2,3d]pyrimidine 2-n-Butylmercapto-4-amino-6-hydroxy-pyrimidine and bromoacetone are subjected to the reaction treatment in accordance with the foregoing SYNTHESIS EXAMPLE 1, wherein dimethylformamide is used as a solvent for the reaction, and ethanol is used as a solvent for recrystallization. There is thus obtained crystal of the final product in a form of white needle.

Melting point: 120°–122° C.

Elementary analysis of the product having presumptive formula $C_{11}H_{15}N_3OS$ gave the following:

|  | C | H | N |
|---|---|---|---|
| Calculated (%) | 55.68 | 6.37 | 17.71 |
| Found (%) | 55.63 | 6.37 | 17.66 |

The chemical structure of the product was determined in the same manner as in the SYNTHESIS EXAMPLE 1.

SYNTHESIS EXAMPLE 3

Synthesis of 2-methylmercapto-4-amino-5-(p-nitrophenyl)furo[2,3-d]pyrimidine

2-Methylmercapto-4-amino-6-hydroxy-pyridine and p-nitro-ω-bromoacetophenone are subjected to the reaction treatment in accordance with the SYNTHESIS EXAMPLE 1, wherein 1,2-dimethoxyethane is used as a solvent for the reaction, and a mixed solvent of dimethylformamide and ethanol is used as a solvent for recrystallization. There is thus obtained the final product as a yellow fine powder.

Melting point: 201°–203° C.

Elementary analysis of the product having presumptive formula $C_{13}H_{10}N_4O_3S$ gave the following:

|  | C | H | N |
|---|---|---|---|
| Calculated (%) | 51.66 | 3.34 | 18.54 |
| Found (%) | 51.24 | 3.23 | 18.17 |

The chemical structure of the product was determined in the same manner as in the SYNTHESIS EXAMPLE 1.

EXAMPLE I FOR PHARMACEUTICAL PREPARATION

Production of Tablets for Oral Administration

| | |
|---|---|
| 2-Ethylmercapto-4-amino-5-methyl-furo[2,3d]pyrimidine hydrobromide | 25 g |
| Lactose | 30 g |
| Potato starch | 40 g |
| Carboxymethylcellulose | 5 g |
| Magnesium stearate | 0.2 g |

The above ingredients are processed in accordance with the conventional manner to produce 1000 tablets. Each tablet contains 25 mg of 2-ethylmercapto-4-amino-5-methyl-furo[2,3d]pyrimidine hydrobromide.

EXAMPLE II FOR PHARMACEUTICAL PREPARATION

Production of Capsule

| | |
|---|---|
| 2-Methylmercapto-4-amino-5-methyl-furo[2,3d]pyrimidine hydrobromide | 5000 mg |
| Corn starch | 1000 mg |
| Crystalline cellulose | 5000 mg |
| Talk | 20 mg |

The above ingredients are processed in accordance with the conventional manner to produce 100 capsules. Each capsule contains 50 mg of 2-methylmercapto-4-amino-5-methyl-furo[2,3d]pyrimidine hydrobromide.

EXAMPLE III FOR PHARMACEUTICAL PREPARATION

Production of Ampoule for Injection

| | |
|---|---|
| 2-Ethylmercapto-4-amino-5-methyl-furo[2,3d]pyrimidine hydrobromide | 25 g |
| Hydrogenated castor oil of polyoxyethylene | 50 g |
| Distilled water for injection | Make up the total volume to 10 litres |

The above ingredients are processed in accordance with the conventional manner to produce ampoules for injection.

Each ampoule contains 5 mg of 2-ethylmercapto-4-amino-5-methyl-furo[2,3d]pyrimidine hydrobromide.

What is claimed is:

1. A member selected from the group consisting of (a) a compound of the formula:

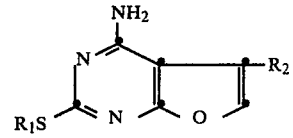

wherein $R_1$ represents lower alkyl of 1 to 4 carbon atoms, lower alkenyl of 2 to 4 carbon atoms, benzyl, phenethyl, or phenylpropyl and $R_2$ represents lower alkyl of 1 to 4 carbon atoms, unsubstituted phenyl or phenyl mono-substituted by carboxyl, methylsulfonyl, methoxycarbonyl or nitro, and (b) a corresponding pharmacologically acceptable acid-addition salt thereof, said compound being produced by the process which comprises the steps of reacting with heating up to reflux conditions a 2-substituted-mercapto-4-amino-6-hydroxy-pyrimidine of the formula:

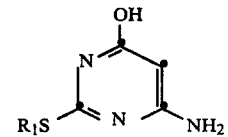

wherein $R_1$ has the same meaning as defined above, with an ω-haloketone of the formula:

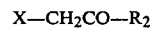

wherein X represents halogen and $R_2$ has the same meaning as defined above, and if desired converting the resulting compound into its pharmacologically acceptable acid-addition salt.

2. A pharmaceutical composition as anti-ulcer, comprising a member selected from the group consisting of (a) a compound of the formula:

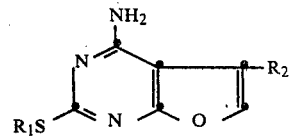

wherein $R_1$ represents lower alkyl of 1 to 4 carbon atoms, lower alkenyl of 2 to 4 carbon atoms, benzyl, phenethyl, or phenylpropyl, and $R_2$ represents lower alkyl of 1 to 4 carbon atoms, unsubstituted phenyl or phenyl mono-substituted by carboxyl, methylsulfonyl, methoxycarbonyl or nitro, and (b) a corresponding pharmacologically acceptable acid-addition salt thereof, said compound being produced by the process which comprises the steps of reacting with heating up to reflux conditions a 2-substituted-mercapto-4-amino-6-hydroxy-pyrimidine of the formula:

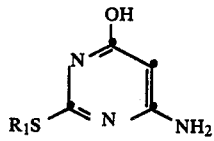

wherein $R_1$ has the same meaning as defined above, with an ω-haloketone of the formula:

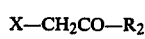

wherein X represents halogen and $R_2$ has the same meaning as defined above, and if desired converting the resulting compound into its pharmacologically acceptable acid-addition salt, and a pharmaceutical carrier.

3. Furo[2, 3d]pyrimidine compound as claimed in claim 1, represented by the chemical formula:

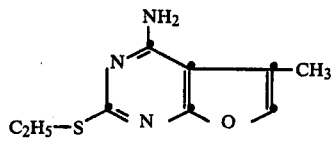

4. Furo[2, 3d]pyrimidine compound as claimed in claim 1, represented by the chemical formula:

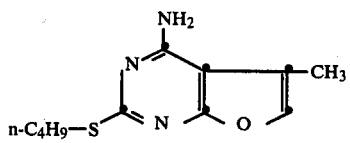

5. Furo[2, 3d]pyrimidine compound as claimed in claim 1, represented by the chemical formula:

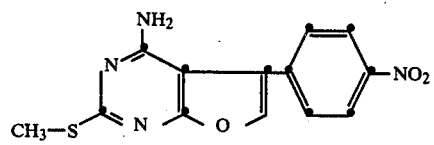

6. Furo[2, 3d]pyrimidine compound as claimed in claim 1, represented by the chemical formula:

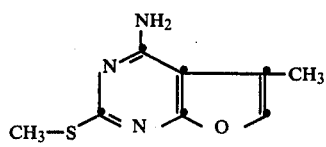

7. Furo[2, 3d]pyrimidine compound as claimed in claim 1 represented by the chemical formula:

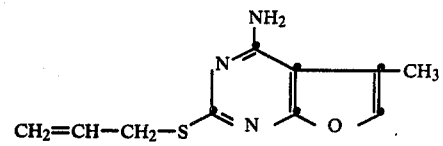

8. Furo[2, 3d]pyrimidine compound as claimed in claim 1, represented by the chemical formula:

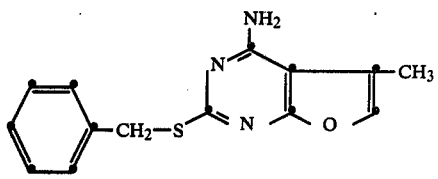

9. Furo[2, 3d]pyrimidine compound as claimed in claim 1, represented by the chemical formula:

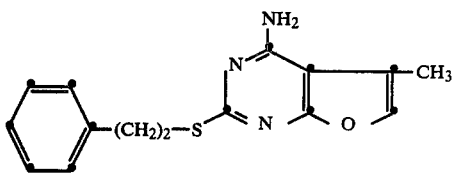

10. Furo[2, 3d]pyrimidine compound as claimed in claim 1, represented by the chemical formula:

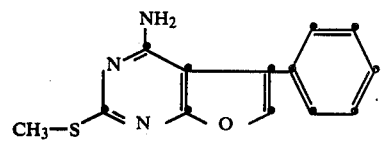

11. Furo[2, 3d]pyrimidine compound as claimed in claim 1, represented by the chemical formula:

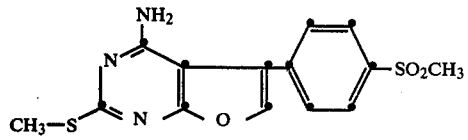

12. Furo[2, 3d]pyrimidine compound as claimed in claim 1, represented by the chemical formula:

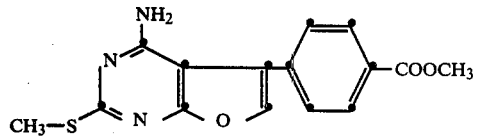

13. Furo[2, 3d]pyrimidine compound as claimed in claim 1, represented by the chemical formula:

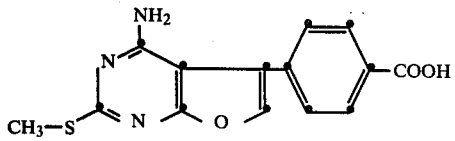

14. Furo[2, 3d]pyrimidine compound as claimed in claim 1, represented by the chemical formula:

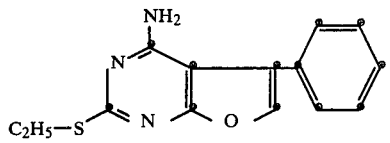

15. Furo[2, 3d]pyrimidine compound as claimed in claim 1, represented by the chemical formula:

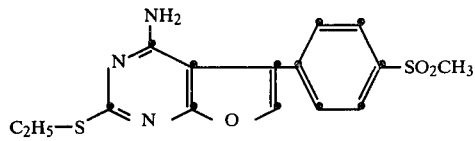

16. A pharmaceutical composition as anti-ulcer as claimed in claim 2, wherein furo[2, 3d]pyrimidine compound is represented by the following chemical formula:

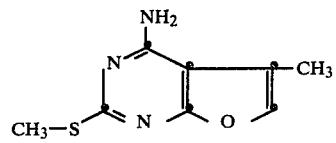

17. A pharmaceutical composition as anti-ulcer as claimed in claim 2, wherein furo[2, 3d]pyrimidine compound is represented by the following chemical formula:

(structure with $NH_2$, $CH_3-S$, N, O, $CH_3$)

18. A pharmaceutical composition as anti-ulcer as claimed in claim 2, wherein furo[2, 3d]pyrimidine compound is represented by the following chemical formula:

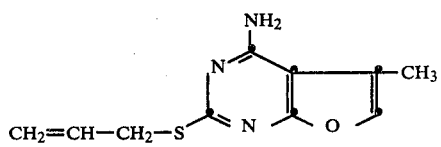

* * * * *